(12) United States Patent
Harris et al.

(10) Patent No.: US 6,187,765 B1
(45) Date of Patent: Feb. 13, 2001

(54) MOMETASONE FUROATE SUSPENSIONS FOR NEBULIZATION

(75) Inventors: David Harris, New Providence; Joel A. Sequeira, Edison; Imtiaz A. Chaudry, North Caldwell, all of NJ (US)

(73) Assignee: Schering Corporation, Kenilworth, NJ (US)

( * ) Notice: Under 35 U.S.C. 154(b), the term of this patent shall be extended for 0 days.

(21) Appl. No.: 09/167,512

(22) Filed: Oct. 6, 1998

Related U.S. Application Data

(60) Provisional application No. 60/061,633, filed on Oct. 9, 1997.

(51) Int. Cl.[7] .............................. A61K 31/58; A61K 9/00
(52) U.S. Cl. ..................... 514/172; 514/958; 514/826; 424/43; 424/45
(58) Field of Search ..................................... 514/958, 826, 514/172; 424/43, 45

(56) References Cited

U.S. PATENT DOCUMENTS

| | | | |
|---|---|---|---|
| 5,192,528 | * | 3/1993 | Radhakrishnan et al. ............. 424/45 |
| 5,837,699 | * | 11/1998 | Sequeira et al. ..................... 514/169 |
| 5,889,015 | * | 3/1999 | Sequeira et al. ..................... 514/172 |

FOREIGN PATENT DOCUMENTS

WO 9204365 * 3/1992 (WO).

* cited by examiner

*Primary Examiner*—Thurman K. Page
*Assistant Examiner*—Amy E Pulliam
(74) *Attorney, Agent, or Firm*—Robert A. Franks

(57) ABSTRACT

An aqueous nebulizer suspension contains water, mometasone furoate monohydrate, a nonionic surfactant, a soluble salt and optionally a pH buffer. The suspension may be prepared by ultrasonication or jet milling techniques.

21 Claims, 1 Drawing Sheet

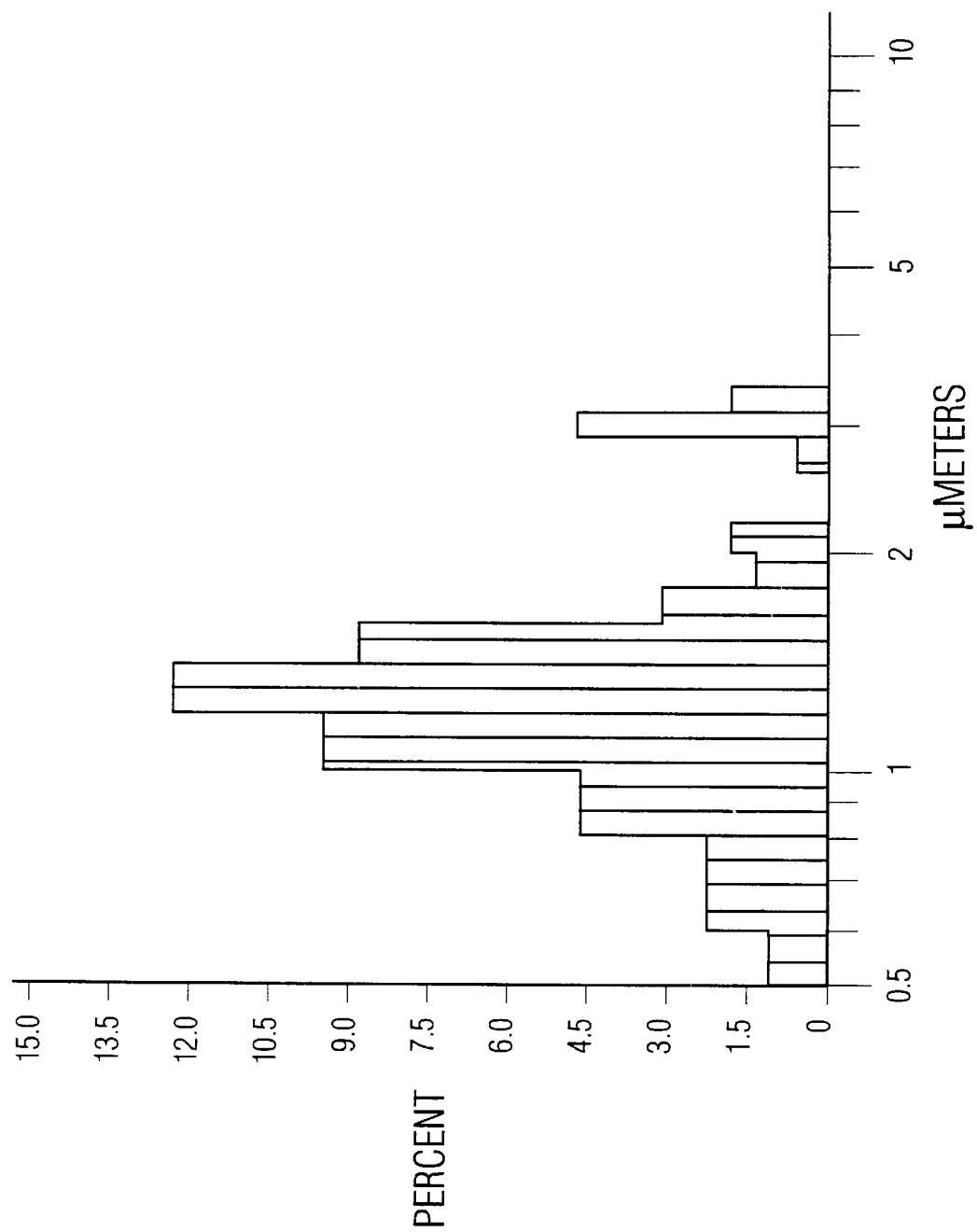

MOMETASONE FUROATE SUSPENSIONS FOR NEBULIZATION

CROSS-REFERENCE TO RELATED APPLICATION

This application claims the benefits under 35 U.S.C. § 119(e) from provisional application 60/061,633 filed Oct. 9, 1997.

INTRODUCTION TO THE INVENTION

The present invention relates to aqueous suspensions of water-insoluble pharmaceutical substances, and more particularly to suspensions of substances intended for inhalation therapy.

Use of inhaled therapeutic substances has become common for the treatment of airway disorders, such disorders including, without limitation thereto, asthma, infections, emphysema and various inflammatory conditions. Substances commonly delivered to the lower airway surfaces, that is, the trachea, bronchial tree and lungs, by oral or nasal inhalation include bronchodilators, corticosteroids, anti-infectives and anti-inflammatory medicaments. Various methods have been used for such delivery, including pressurized metered dose inhalers, dry powder inhalers and nebulizers.

Nebulizers are considered to be instruments generating very fine particles of a liquid in a gas. As is very well known, particles intended for treatment of the lower airway, i.e., the bronchial tree or the lungs, will generally be less than 10 micrometers in the largest dimension, to prevent unwanted deposition onto surfaces of the mouth and pharynx, and more preferably will be less than 5 $\mu$m. In addition, particles much smaller than about 0.5 $\mu$m in the largest dimension frequently are not easily deposited at the desired location, and a large fraction of these simply will be exhaled by a patient. For these reasons, it is generally desired to produce particles which average 1–7 $\mu$m in their largest dimension, while preferably minimizing production of particles having sizes either less than about 0.5 or greater than about 10 $\mu$m. The more preferred average particle sizes are in the range of 0.5–5 $\mu$m.

Nebulization, although used more infrequently than other drug delivery techniques, has certain advantages for special patient groups, such as young children and the very infirm. Although somewhat cumbersome equipment is needed and there may be more stringent cleaning requirements than exist for some of the more popular delivery techniques, no particular patient skill or coordination is required: the patient merely needs to breathe normally to introduce the medication into the airway. Thus, treatment can be delivered even to an unconscious patient or an infant. It is also considered an advantage of nebulizers that quantities of moisture are delivered to the airway; this may help to fluidize secretions and tends to increase patient comfort.

The typical nebulized medication is a water-soluble substance which can form relatively dilute aqueous solutions. This is desired, due to the relatively large volumes of solution which will be entrained in an inhaled air stream, and to the very small quantities of drug which will typically be delivered in a single treatment. Handling of a drug solution is quite uncomplicated: a desired volume of a solution (usually aqueous) is either nebulized directly or is measured into a larger volume of sterile water for nebulization.

However, some very useful inhalation drugs have little or essentially no water solubility. Examples of such drugs are corticosteroids, typically administered in the treatment of asthma by inhalation from pressurized metered dose inhalers, either in alcohol solution or as suspended micronized particles, or from dry powder inhalers of various types.

It is also known to form an aqueous suspension of drug particles, for nebulization. Commercial products, which have not been made available in all countries, currently include beclomethasone dipropionate (sold by Glaxo under the trade name BECOTIDE) and budesonide (formulated with a citrate-citric acid buffer and Polysorbate 80 surfactant, and sold by Astra under the trade name PULMICORT). Corticosteroids have also been formulated in liposome suspensions in aqueous media, for nebulizer delivery, as in U.S. Pat. No. 5,192,528.

The therapeutic advantages of the corticosteroid mometasone furoate for treating disorders of the lower airway make this drug a desirable candidate for delivery by nebulization. Since this drug is not soluble in aqueous media, it has become necessary to develop aqueous suspensions for nebulization.

SUMMARY OF THE INVENTION

The invention comprises an aqueous suspension of micronized mometasone furoate monohydrate, also containing a nonionic surfactant, a soluble salt and optionally a pH buffer. Preferred surfactants are those known as polysorbates. The soluble salt may be sodium chloride, in amounts needed to render the solution phase isotonic. When the buffer is present, it preferably will be chosen to maintain a solution pH between about 3 and about 7.

BRIEF DESCRIPTION OF THE DRAWING

FIG. 1 is a graphical representation of results from the experiment of Example 3.

DETAILED DESCRIPTION OF THE INVENTION

Percentages expressed herein are meant to indicate percent by weight, unless the context clearly dictates otherwise.

The suspension formulations of the invention may be delivered to a patient using any of the usual nebulizer devices. Typical commercial nebulizer devices produce dispersions of droplets in gas streams by one of two methods. Jet nebulizers use a compressed air supply to draw up a fluid by venturi action and introduce it into a flowing gas stream, after which the fluid is caused to impact one or more stationary baffles to remove excessively large droplets. Ultrasonic nebulizers use an electrically driven transducer to subject a fluid to high-frequency oscillations, producing a cloud of droplets which can be entrained in a moving gas stream; these devices are less preferred for delivering suspensions. There are hand-held nebulizers which atomize the fluid with a squeeze bulb air supply, but the more widely used equipment incorporates an electrically powered compressor or connects to a cylinder of compressed gas. Although the various devices which are commercially available vary considerably in their delivery efficiency for a given medicament, they all are useful for the treatment of the present invention; it is necessary for the prescriber to specify an exact amount of medicament formulation which is to be charged to each particular device, since their respective outputs of respirable droplets are far from identical.

Suspension formulations suitable for nebulization must, of course, contain solid particles of a respirable size (e.g., preferably averaging less than about 5 $\mu$m in the largest dimension and more preferably averaging less than about 2 µm) and must maintain their suspended particle size distribution during storage. In addition, the particle-containing droplets formed during nebulization of the formulations must have appropriate sizes for deposition in the desired area of the respiratory system.

Since the formulations of the invention are to be inhaled, it is necessary that they be free of pathogenic organisms. Thus, they may be prepared and handled under sterile conditions, or may be sterilized before or after packaging. In addition, or in lieu of sterilization, a preservative may be incorporated to minimize the possibility of microbial contamination. In addition, all components of the formulations must be chosen for inhalation safety, as the treated tissues are quite sensitive to irritants; it is commonly known that many of the common preservatives have a considerable potential for causing irritation.

The inventive formulations comprise water, mometasone furoate monohydrate, a nonionic surfactant, a soluble salt and optionally a pH buffer.

Water for use in the formulations should meet or exceed the applicable regulatory requirements for use in inhaled drugs. Specifications established by the *United States Pharmacopoeia* for "Sterile Water for Injection" or "Sterile Water for Inhalation" are examples of water suitable for use to prepare formulations of the invention.

Mometasone furoate is a corticosteroid having the chemical name 9α,21-Dichloro-11β,17-dihydroxy-16α-methylpregna-1,4-diene-3,20-dione 17-(2-furoate), and is currently marketed by Schering Corporation in cream and lotion formulations for the treatment of dermatologic conditions. Information concerning the preparation and properties of mometasone furoate is given in U.S. Pat. 4,472,393. This compound may be used to prepare mometasone furoate monohydrate for use in the present invention. Information concerning the preparation and properties of mometasone furoate monohydrate is given in PCT International Application WO 92/04365.

In general, the concentration of mometasone furoate included in the suspension formulation will depend upon the dose to be delivered to the patient, ease of handling and the characteristics of the nebulizer equipment, as the devices vary considerably in their suspension capacities and nebulization efficiencies. Typical suspensions may contain as much as about 5 mg/mL of mometasone furoate, although lower concentrations, such as 50 µg/mL to 1 mg/mL are more customary for most equipment.

Surfactants are frequently categorized by their chemical nature, i.e., as cationic, anionic or nonionic. Cationic surfactants, such as cetyl pyridinium chloride, and anionic surfactants, such as docusate sodium, do not appear to provide proper dispersions of particles in the formulations.

Many nonionic surfactants are suitable for maintaining the particulate suspensions of the invention. These include surfactants identified as "polysorbates" in the CTFA *International Cosmetic Ingredient Dictionary*; such surfactants are mixtures of fatty acid esters (predominately monoesters) of sorbitol and sorbitol anhydrides, condensed with ethylene oxide. Although these surfactants vary widely in their hydrophilic-lipophilic balance ("HLB") numbers, they all appear to function well in the invention.

Commercially available polysorbates which are useful in the invention include those listed in the following table, which shows the CTFA designation (Polysorbate number), identity of the fatty acid used to produce the material and the number of moles of ethylene oxide reacted with each mole of ester. Compositions identified with an asterisk are predominately triesters.

| Polysorbate | Acid | Moles EtO |
| --- | --- | --- |
| 20 | Lauric | 20 |
| 21 | Lauric | 4 |
| 40 | Palmitic | 20 |
| 60 | Stearic | 20 |
| 61 | Stearic | 4 |
| 65* | Stearic | 20 |
| 80 | Oleic | 20 |
| 81 | Oleic | 5 |
| 85* | Oleic | 20 |

In general, Polysorbate surfactants will be present in a formulation at about 50 to 500 µg/mL. When the surfactant concentration is below about 20 µg/mL, the particles tend to form cakes which are not easily redispersed.

Useful surfactants also include the "Poloxamers," which are block polymers of polyoxyethylene and polyoxypropylene, generally corresponding to the following formula:

$$HO(CH_2CH_2O)_x[CH(CH_3)CH_2O]_y(CH_2CH_2O)_zH$$

Representative commercially available poloxamer surfactants are listed in the following table, wherein the CTFA designation (Poloxamer number) and average values of x, y and z are given.

| Poloxamer | x | y | z |
| --- | --- | --- | --- |
| 101 | 2 | 16 | 2 |
| 105 | 11 | 16 | 11 |
| 108 | 46 | 16 | 46 |
| 122 | 5 | 21 | 5 |
| 123 | 7 | 21 | 7 |
| 124 | 11 | 21 | 11 |
| 181 | 3 | 30 | 3 |
| 182 | 8 | 30 | 8 |
| 183 | 10 | 30 | 10 |
| 184 | 13 | 30 | 13 |
| 185 | 19 | 30 | 19 |
| 188 | 75 | 30 | 75 |
| 212 | 8 | 35 | 8 |
| 215 | 24 | 35 | 24 |
| 217 | 52 | 35 | 52 |
| 231 | 6 | 39 | 6 |
| 234 | 22 | 39 | 22 |
| 235 | 27 | 39 | 27 |
| 237 | 62 | 39 | 62 |
| 238 | 97 | 39 | 97 |
| 282 | 10 | 47 | 10 |
| 284 | 21 | 47 | 21 |
| 288 | 122 | 47 | 122 |
| 331 | 7 | 54 | 7 |
| 333 | 20 | 54 | 20 |
| 334 | 31 | 54 | 31 |
| 335 | 38 | 54 | 38 |
| 338 | 128 | 54 | 128 |
| 401 | 6 | 67 | 6 |
| 402 | 13 | 67 | 13 |
| 403 | 21 | 67 | 21 |
| 407 | 98 | 67 | 98 |

Poloxamer surfactants are used at concentrations similar to those for the Polysorbates, although certain members are useful at concentrations up to about 1 mg/mL.

In general, the chosen surfactant should not materially increase the viscosity of the suspension formulation, since the efficiency of the nebulization process is particularly sensitive to viscosity. Many nonionic surfactants are useful for preparing inhalation and/or injectable drug formulations, and any of these should be suitable for use in the present invention.

The formulations further include a soluble salt. This salt performs at least two functions: it minimizes the effects of the inhaled formulation on the normal cell fluid balance of airway cells and also stabilizes the suspension of medicament. For the first function, it is preferred to use sufficient salt concentrations to render the formulation isotonic; sodium chloride and potassium chloride are preferred for this purpose. It has been found that adequate suspension stability is produced by isotonic concentrations (i.e., about 0.9 weight percent) of sodium chloride, although concentrations about 0.2 to about 2 weight percent are useful. Any physiologically compatible alkali metal or alkaline earth metal soluble salt can be used in the present invention.

Optionally, the formulations will contain a pH buffer, to maintain the formulation pH between about 3 and about 7. It has been found that stability of the drug (as measured by the absence of degradation reaction products) in suspension is improved by maintaining pH conditions below about 6. For reasons of tissue compatibility, excessively acidic products are not desired, so the pH should not be made to be below about 3. Some experimentation may be needed to qualify specific buffers for use in the invention: phosphate buffers in concentrations of 1 to 50 millimolar do not appear to adequately prevent caking of the particulates in the suspension when there is no added soluble salt. A citrate-citric acid buffer, maintaining pH between about 4 and about 5, has been used with particularly good effect for both maintaining pH during storage and preventing any particulate caking in the absence of soluble salts.

The citrate-citric acid buffer may be present in suspension formulations at concentrations at least about 2 and up to about 50 millimolar. While the literature has some reports of cough being induced by such buffer systems, this seems to occur primarily at the 150–200 millimolar level, although one report attributed cough to only a 35 millimolar concentration.

Sterility or adequate antimicrobial preservation of the final packaged formulation is needed for patient protection. The use of antimicrobial preservatives is less desirable, since certain of these have been associated with adverse clinical effects, such as bronchospasm. Alternative processes which may be considered for achieving sterility usually will not include sterilization steps for the micronized drug substance or formulation, since it has been found that the drug undergoes degradation under the influence of gamma-ray irradiation and sterilizing heat conditions. Sterilization by filtration ordinarily will not be feasible, due to the suspension nature of the formulation. Thus, it is preferred to produce the mometasone furoate monohydrate under sterile conditions, conduct the drug micronization in a sterile environment, and perform a sterile packaging operation.

Methods are known for reducing particle sizes into the micrometer range, including mechanical milling, application of ultrasonic energy and other techniques. Mechanical milling frequently generates high surface temperatures on the particles, and this is undesirable for mometasone furoate monohydrate which tends to lose some part of its hydration under the influence of high temperatures. Ultrasonic techniques are quite slow in their action, generally requiring very long processing times, but are capable of producing acceptable suspensions.

Suspensions of drug particles can rapidly undergo particulate size reduction when subjected to "jet milling" (high pressure particle in liquid milling) techniques. A presently preferred jet milling procedure for producing the formulations of the invention involves the use of the "Microfluidizer" system sold by Microfluidics International Corporation of Newton, Mass., U.S.A. This device divides a fluid stream, flowing under high pressures (up to about 40,000 pounds per square inch, or $2.76 \times 10^8$ newton/meter$^2$), between two separate microchannel paths and then recombines them from generally perpendicular directions to create very high shear, impact and cavitation forces. By continuously recirculating suspensions through the system for a predetermined time period, it is possible to reproducibly create desired distributions of micron- and submicron-sized particles. Since the particles are always completely surrounded by liquid, their surfaces will not develop high temperatures under the influence of the size reduction forces, and the hydration water in the drug crystals will remain intact. Other useful equipment which utilizes related technology is available from Avestin Inc., Ottawa, Ontario, Canada.

The following examples are provided to further illustrate and explain certain aspects of the invention, and are not intended to limit the scope of the invention, as defined by the appended claims, in any manner.

EXAMPLE 1

Sterile mometasone furoate monohydrate is prepared by a procedure including the following steps:

(1) charge 250 grams mometasone furoate to a dissolution vessel containing 4250 mL of acetone, and mix to form a clear solution;

(2) pump the solution through a sterilizing filter, such as a filtration medium having pores not exceeding 0.2 μm in diameter, into a sterile precipitation vessel equipped with means for stirring and means for heating the contents (note that sterile equipment and a sterile environment must be used for all subsequent steps);

(3) heat the sterile solution to about 45–50° C. and slowly add, over about 15 minutes, 1000 mL of sterile purified water while maintaining the temperature;

(4) while maintaining the elevated temperature, slowly add an additional 750 mL of the water, with stirring over about 30 minutes;

(5) continue the stirring and maintain the temperature for an additional 30 minutes, during which a precipitate will begin to form;

(6) slowly add an additional 5250 mL of the water over about 60 minutes, while maintaining a rapid stirring and the elevated temperature;

(7) continue stirring at the elevated temperature for about 60 minutes;

(8) cool the mixture to ambient temperature, with continued stirring;

(9) filter the precipitate (mometasone furoate monohydrate) and wash it with two 500 mL portions of the sterile purified water; and

(10) dry in a vacuum oven at 30–35° C. for 12–24 hours.

The dried sterile mometasone furoate monohydrate product should have a water content, as measured by a standard Karl Fischer titration, of 3.3 percent by weight and contains 96.7 percent by weight mometasone furoate.

EXAMPLE 2

A 40 liter batch of a sterile aqueous suspension of mometasone furoate monohydrate is prepared using the following procedure:

(1) sequentially charge 2.0 grams of Polysorbate 80, 7.24 grams of citric acid monohydrate and 13.4 grams of sodium citrate dihydrate to about 1000 grams of purified water in a vessel equipped for stirring, stir to form a solution having a pH of 4.5±0.5, add additional purified water to make 1315 grams of solution and filter the solution under pressure through a 0.2 μm sterilizing filter into a sterile recirculation vessel, equipped for stirring;

(2) add 360 grams of sodium chloride to about 1800 grams of purified water, stir to dissolve, add additional purified water to make 2000 grams of solution and filter under pressure through a 0.2 μm sterilizing filter into a sterile vessel;

(3) add 21.73 grams of mometasone furoate monohydrate, prepared as in Example 1, to the sterile solution of step (1) and commence stirring the vessel contents to form a suspension;

(4) pass the mixture of the preceding step through a sterilized Model 210B-EH pilot-scale Microfluidizer operating at 17500±500 pounds per square inch ($1.21 \times 10^8$ newton/meter$^2$±$3.45 \times 10^6$ newton/meter$^2$) gauge pressure for 40±5 minutes while returning the Microfluidizer discharge into the stirred recirculation vessel;

(5) transfer the micronized mometasone furoate suspension from the recirculation vessel to the vessel of step (2);

(6) rinse the Microfluidizer with sterile purified water and add the rinse water to the suspension formed in the preceding step, then add a sufficient additional quantity of the water to form a suspension weighing 40100 grams; and (7) fill individual sterile containers with a desired amount of suspension (containing 0.5 mg of mometasone furoate per milliliter and having a specific gravity of 1.003 g/cm$^3$) for use in a nebulizer.

The weight for the mometasone furoate monohydrate includes a 5 percent overcharge to compensate for manufacturing losses.

EXAMPLE 3

Using the procedure of the preceding example, a suspension is prepared which has the following composition and a pH about 4.5:

| | |
|---|---|
| Mometasone furoate * | 599 μg |
| Polysorbate 80 | 50 μg |
| Citric acid monohydrate | 181 μg |
| Sodium citrate dihydrate | 335 μg |
| Sodium chloride | 9 mg |
| Water for injection, USP | to make 1 mL |

* From mometasone furoate monohydrate

A particle size distribution is determined for the suspension by a laser light scattering technique. A Malvern 2600 instrument, manufactured by Malvern Instruments, Malvern, Worcestershire, United Kingdom, is set up with a liquid flow cell and a 63 mm lens, and operated in its "particle in liquid" mode with water (containing a small amount of Polysorbate 80 as a wetting agent) as the vehicle. Drug suspension is added until an optimum light obscuration is achieved, then the measurements are obtained. Data are calculated and expressed on a volume distribution basis, and are graphically represented as shown in FIG. 1. This suspension has a median particle size of 1.24 μm and a mean particle size of 1.34 μm.

EXAMPLE 4

Commercially available nebulizers are used to determine the drug delivery characteristics for the suspension of the preceding example and two commercial suspension products: BECOTIDE beclomethasone dipropionate suspension (Glaxo) and PULMICORT budesonide suspension (Astra). The nebulizers are WHISPER JET (Marquest Medical Products, Englewood, Colo., U.S.A.) and PARI JET (PARI Respiratory Equipment, Inc., Richmond, Va., U.S.A.). Suspensions are placed into the nebulizers in 3 mL amounts, and the equipment is connected to a compressor and operated according to the manufacturers' instructions. Nebulized drug is directed into the top of a 500 mL separatory funnel containing a 1 gram plug of cotton, and the lower outlet of the funnel is connected to a vacuum line. After the nebulizer becomes dry, the vacuum line is disconnected and the funnel (with the plug) is washed with 25 mL of a solvent for the drug (e.g., methanol), which is then collected and analyzed for the drug by high performance liquid chromatography to determine the percentage of originally charged drug which was delivered to the funnel.

Results are obtained as follows, where the values are averages of four determinations:

| | Percent Delivered | |
|---|---|---|
| Product | Pari Jet | Whisper Jet |
| Example 3 | 32.9 | 23.6 |
| Becotide | 23.5 | 13.4 |
| Pulmicort | 31.9 | 18.1 |

EXAMPLE 5

As in preceding Example 3, the following suspension formulations are prepared, each containing sufficient sterile water to make a final volume of 1 mL:

| Formula | 5A | 5B | 5C |
|---|---|---|---|
| Mometasone furoate, μg | 250 | 500 | 500 |
| Polysorbate 80, μg | 50 | 500 | 50 |
| Citric acid monohydrate, μg | 181 | 181 | 80 |
| Sodium Citrate dihydrate, μg | 335 | 335 | 470 |
| Sodium chloride, mg | 9 | 9 | 9 |

The mometasone furoate content is provided by mometasone furoate monohydrate.

EXAMPLE 6

As in preceding Example 3, the following suspension formulations are prepared, each containing sufficient sterile water to make a final volume of 1 mL:

| Formula | 6A | 6B | 6C |
|---|---|---|---|
| Mometasone furoate, μg | 500 | 500 | 750 |
| Polysorbate 80, μg | 50 | 50 | 50 |
| Citric acid monohydrate, μg | 294 | 181 | 181 |
| Sodium Citrate dihydrate, μg | 174 | 335 | 335 |
| Sodium chloride, mg | 9 | 4.5 | 18 |

The mometasone furoate content is provided by mometasone furoate monohydrate.

What is claimed is:

1. A nebulizer suspension consisting essentially of water, mometasone furoate monohydrate, a nonionic surfactant, about 0.2 to about 2 weight percent of sodium chloride or potassium chloride and, optionally, a pH buffer.

2. The suspension of claim 1, wherein mometasone furoate monohydrate comprises about 50 micrograms to about 5 milligrams, per milliliter.

3. The suspension of claim 1, wherein the surfactant comprises a Polysorbate surfactant.

4. The suspension of claim 1, wherein the surfactant comprises Polysorbate 80.

5. The suspension of claim 1, wherein the surfactant comprises a Poloxamer surfactant.

6. The suspension of claim 1, wherein the surfactant comprises about 50 micrograms to about 1 milligram, per milliliter.

7. The suspension of claim 1, wherein the salt comprises sodium chloride.

8. A method for treating airway disorders, comprising administering by nebulization to surfaces of the airway a treatment-effective amount of the suspension of claim 1.

9. The suspension of claim 1, which includes a pH buffer.

10. The suspension of claim 9, wherein the buffer comprises a citric acid-citrate buffer.

11. The suspension of claim 9, wherein the buffer maintains aqueous phase pH values about 3 to about 7.

12. The suspension of claim 9, wherein the buffer maintains aqueous phase pH values about 3 to about 6.

13. The suspension of claim 9, wherein the buffer maintains aqueous phase pH values about 4 to about 5.

14. The suspension of claim 1, wherein solid particles have average sizes less than about 5 $\mu$m.

15. The suspension of claim 1, wherein solid particles have average sizes less than about 2 $\mu$m.

16. A process for producing a nebulizer suspension, comprising combining ingredients consisting essentially of water, mometasone furoate monohydrate, a nonionic surfactant, about 0.2 to about 2 weight percent of sodium chloride or potassium chloride and, optionally, a pH buffer and subjecting the combination to particle size reduction by ultrasonication or by jet milling.

17. The process of claim 16, wherein the combination includes a pH buffer.

18. The process of claim 16, wherein particle size reduction is continued to produce solid particles having sizes less than about 10 $\mu$m.

19. The process of claim 16, wherein particle size reduction is continued to produce solid particles having average sizes less than about 5 $\mu$m.

20. The process of claim 16, wherein particle size reduction is continued to produce solid particles having average sizes less than about 2 $\mu$m.

21. A method for treating airway disorders, comprising administering by nebulization to surfaces of the airway a treatment-effective amount of a suspension prepared by the process of claim 16.

* * * * *